US012799184B2

(12) United States Patent
Mooney et al.

(10) Patent No.: US 12,799,184 B2
(45) Date of Patent: Nov. 17, 2026

(54) METHOD OF PREPARING FIBRONECTIN CONCENTRATES FROM CRYOPRECIPITATE ANTI-HEMOLYTIC FACTOR

(71) Applicant: Oklahoma Blood Institute, Oklahoma City, OK (US)

(72) Inventors: Charles Mooney, Oklahoma City, OK (US); Jennifer Chain, Oklahoma City, OK (US)

(73) Assignee: OKLAHOMA BLOOD INSTITUTE, Oklahoma City, OK (US)

( * ) Notice: Subject to any disclaimer, the term of this patent is extended or adjusted under 35 U.S.C. 154(b) by 596 days.

(21) Appl. No.: 18/098,257

(22) Filed: Jan. 18, 2023

(65) Prior Publication Data

US 2023/0235021 A1 Jul. 27, 2023

Related U.S. Application Data

(60) Provisional application No. 63/303,751, filed on Jan. 27, 2022.

(51) Int. Cl.

| | |
|---|---|
| ***C07K 14/745*** | (2006.01) |
| ***C07K 1/30*** | (2006.01) |
| ***C07K 1/34*** | (2006.01) |

(52) U.S. Cl.

CPC .............. *C07K 14/745* (2013.01); *C07K 1/30* (2013.01); *C07K 1/34* (2013.01)

(58) Field of Classification Search

None

See application file for complete search history.

(56) References Cited

U.S. PATENT DOCUMENTS

| | | | | |
|---|---|---|---|---|
| 7,087,577 B2 * | 8/2006 | Benedict | ................ | A61K 38/30 514/8.8 |
| 7,670,595 B2 * | 3/2010 | Gillies | .................... | A61P 37/02 536/23.4 |
| 8,557,232 B2 * | 10/2013 | Gillies | .................... | A61P 35/00 424/134.1 |

FOREIGN PATENT DOCUMENTS

| | | | | |
|---|---|---|---|---|
| WO | WO-8912065 A1 * | 12/1989 | ............... | C07K 1/16 |

OTHER PUBLICATIONS

Horowitz et al. (Transfusion, vol. 24, Issue 4, Jul. 1984, pp. 357-362).*

* cited by examiner

*Primary Examiner* — Hope A Robinson

(74) *Attorney, Agent, or Firm* — Barnes & Thornburg LLP

(57) ABSTRACT

Fibronectin enhances growth of adherent cells in culture. Methods herein involve producing human-derived fibronectin concentrate from the cryo-precipitation of plasma. Fibronectin concentrates from many donors are pooled, filtered, and irradiated, followed by adjustment of the fibronectin concentration to fit individual customer needs. Aliquots of the final fibronectin concentrate product can be used in cell therapy and regenerative medicine cell cultures.

18 Claims, 3 Drawing Sheets

METHOD OF PREPARING FIBRONECTIN CONCENTRATES FROM CRYOPRECIPITATE ANTI-HEMOLYTIC FACTOR

CROSS REFERENCE TO RELATED APPLICATION

This application claims the benefit of U.S. Provisional Patent Application No. 63/303,751 filed on Jan. 27, 2022, which is hereby incorporated by reference.

FIELD

The present invention is a method of preparing a fibronectin concentrate from human plasma that can be used in culturing cellular therapy and regenerative medicine products.

BACKGROUND

Plasma is made of mostly water, but also contains dissolved proteins (including fibronectin), electrolytes, glucose, clotting factors, antibodies, and hormones. Plasma is separated from whole blood (WB) units using a centrifugal force to create a division between the red blood cells (RBCs), white blood cells (WBCs), and plasma fractions of the unit. Centrifuging the WB unit forces the RBCs toward the bottom of the container, while plasma remains at the top and the WBCs in between the other two layers. Pressure is applied to the centrifuged WB bag to push plasma into an empty bag attached to the blood pack. Plasma is also obtained through apheresis procedures, where plasma is extracted from blood and pushed into a collection bag and the remaining portions of the blood are returned to the donor. Donated plasma is typically frozen until it is needed for transfusion.

Frozen plasma can be thawed at refrigerated temperatures or body temperatures. When thawed at refrigerated temperatures, the proteins and clotting factors in the plasma with the highest molecular weights become solid, fall out of solution, and settle to the bottom of the liquid plasma product. These proteins and clotting factors are separated from the remaining portion of the plasma by centrifugation, then used for therapeutic applications, including transfusion to patients. When used for transfusion, this product is called "cryoprecipitate anti-hemolytic factor (AHF)". Cryoprecipitate AHF contains fibrinogen, clotting factor VIII (also known as anti-hemophilic factor), fibronectin, clotting factor XIII and von Willebrand factor. The product acquired its name because it was first used to treat patients with hemophilia who have a hereditary factor VIII deficiency. With the invention of lyophilized factor VIII, it is no longer used for this purpose. Most often today, cryoprecipitate AHF is therapeutically used as a source of fibrinogen.

SUMMARY

The present disclosure provides a method of preparing fibronectin concentrates from cold precipitates found in plasma. Fibronectin, also called cold-insoluble globulin, is a blood plasma protein produced by the liver. The primary function of this protein is to promote cell adhesion and plays an important role in wound healing.

Whole blood (WB) is collected from a donor and centrifuged to separate plasma from the cellular components of blood. Alternatively, plasma can be collected using an apheresis device. With apheresis, a needle is inserted into the donor's arm, then with a peristaltic pump and a closed system disposable collection kit, whole blood is withdrawn into the device. The device separates plasma from cellular components using centrifugation. With the needle still in the donor's arm, the device returns the other blood components to the donor. This process is repeated until the desired volume of plasma is collected.

Plasma, whether derived from a WB unit or an apheresis procedure, is frozen and stored at temperatures at or below −20° C. Generally, most such freezing temperatures will work unless they are low enough to be detrimental to the plasma. For example, the WB unit can be stored at a temperature from −20° C. to −100° C.

Frozen plasma (whole blood fresh frozen plasma, whole blood plasma frozen within 24 hours of collection, apheresis fresh frozen plasma, or apheresis plasma frozen within 24 hours of collection) in this method is placed in a refrigerator to thaw at low temperatures over a period of hours. Generally, this thawing is at temperatures below 15° C. but above 0° C. over a time period sufficient to achieve complete thawing of the plasma, for example, the time period may be at least 4 hours, and may be up to 24 hours or even longer, if needed. A typical thawing would be carried out at 2-8° C. over a period of 6 to 12 hours. The exact time required for complete thawing will vary from batch to batch.

When plasma is thawed at cold temperatures, the dissolved high molecular weight proteins and clotting factors become solids and fall (precipitate) out of the plasma solution and pool to the bottom of the container. The solids that are formed at the bottom of the plasma container are combined with the precipitate from other donors to create a pool of fibronectin-rich material.

The fibronectin-rich material is resuspended in plasma and the solid fibrinogen portions are removed when passed through a filter. After filtration, pools are exposed to radiation.

After irradiation, fibronectin levels of the pooled, filtered, and irradiated fibronectin-rich material are measured. After measurement, optimization of the fibronectin concentration occurs. If the concentration is too low, then irradiated cryoprecipitate AHF is added to the pool. If the fibronectin level is too high, then filtered, irradiated plasma is added to the pool.

The concentration-optimized, pooled, filtered, and irradiated fibronectin concentrate is aliquoted into small volumes, typically 15 mL, but can range from 1 mL to 100 mL, with fibronectin concentrations ranging from 1 to 5 mg/mL.

The fibronectin concentrate product is used to generate a 3-dimensional matrix to promote the adhesion of cells in cultures.

DETAILED DESCRIPTION

Figure 1:
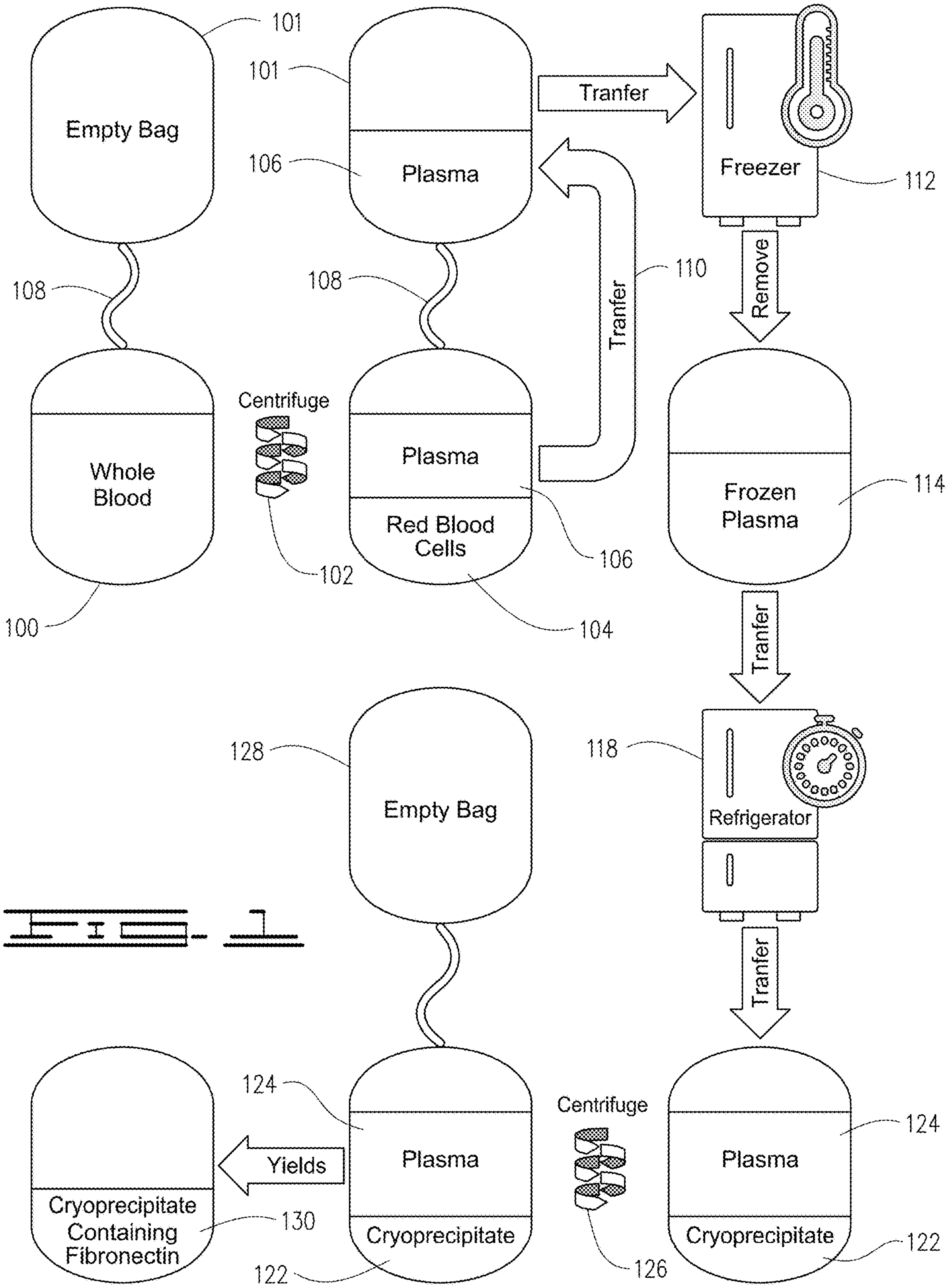
FIG. 1 is a schematic of preparing fibronectin-rich material.

The present disclosure may be understood more readily by reference to these detailed descriptions. Numerous specific details are set forth to provide a thorough understanding of the various embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

As utilized in accordance with the present disclosure, the following terms, unless otherwise indicated, shall be understood to have the following meanings: the use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements, or method steps.

Throughout this disclosure, the terms "about", "approximate", and variations thereof, are used to indicate that a value includes the inherent variation or error for the device, system, the method being employed to determine the value, or the variation that exists among the donors.

Therapies using modified human cells are used as biological drugs to treat a multitude of diseases and conditions. Cell therapies and regenerative medicine products made from cells that naturally grow while attached to a surface benefit from a 3-dimensional growth matrix created with the addition of fibronectin prior to initiating the cell culture process. Pretreating the growth surface with fibronectin has been shown to increase cell adhesion and expansion during culture. Heterogenicity of fibronectin concentrates is important to ensure the desired levels of fibronectin are achieved and can be standardized with each batch produced. This disclosure describes methods using cold precipitate to prepare a source of fibronectin to enhance cell adhesion in cultures used to make cellular therapy and regenerative medicine products. The present disclosure may be understood more readily by referencing these detailed descriptions and FIG. 1, FIG. 2 and FIG. 3.

As described above, plasma may be obtained from whole blood (WB) donation from donors or from plasma donations from donors by using an apheresis device. When a WB donation occurs, donors have their arm prepared for phlebotomy. Once the donor's arm is prepared, venipuncture occurs and a blood pack (a blood collection bag with a series of plastic tubing and empty bags attached) is used to collect a WB unit.

The collected WB is packed on ice and transported to the laboratory for processing into individual blood components such as packed red blood cells (RBCs), plasma, platelets, buffy coat (white blood cells (WBCs)), and cryoprecipitate anti-hemolytic factor (cryoprecipitate AHF).

As illustrated in FIG. 1, a fibronectin-rich material is prepared from whole blood. The WB unit is first separated into plasma and RBC. For example, the blood and blood bag 100 are placed in a centrifuge 102, which is operated at speed and time sufficient to separate the blood into an RBC layer 104 and plasma layer 106. For example, the centrifuge can be operated at about 4500 RPM for about 8 minutes to separate the blood into layers. After centrifugation, the bag is placed into a press that applies external pressure to the bag. A physical barrier located in the plastic tubing 108 connected to the layered blood bag 100 and an empty plastic bag 101 is broken, opening a sterile fluid path between the two bags. The pressure applied from the press forces plasma through tubing 108 into the empty plastic bag 101 as illustrated by arrow 110. Once the desired amount of plasma has been transferred, the fluid path is closed with a hermetic seal.

Plasma can also be collected using an apheresis device (not shown). The device has a disposable tubing set that is loaded into the device's separation chamber. The tubing set has a series of empty plastic bags and a needle attached. During an apheresis procedure, donors have their arm prepared for phlebotomy. Following venipuncture, the apheresis procedure is initiated and blood is pulled into the separation chamber where it is subjected to a centrifugal force. With centrifugation, blood is separated inside the tubing set into layers: RBCs, WBCs, and plasma. The apheresis device is programmed to collect one or more of the blood layers. The desired layer is collected in small volumes and pushed by a peristaltic pump into the collection bag. At the same time, the layers not collected are returned to the donor using the same needle that was used to withdraw the blood. This intermittent process continues until the desired volume of each layer is collected.

Plasma derived from WB or an apheresis procedure is rapidly frozen 112 to produced frozen plasma 114 and then stored in a freezer/refrigerator at temperatures at or below −20° C., a typical rapid freeze occurs within 60 minutes. Generally, most such freezing temperatures will work unless they are low enough to be detrimental to the plasma. For example, the WB unit can be stored at a temperature from −20° C. to −100° C. Refrigeration storage can be for any suitable or desired time.

Frozen plasma must be thawed before use. If plasma is for infusion to a patient, the plasma is thawed at 37° C. (body temperature); however, if the plasma will be used to make cryoprecipitate AHF in accordance with this disclosure, the unit is moved from the freezer (step 116) into a refrigerator 118 and thawed at low temperatures over a period of hours, for convenience the thawing can be overnight. Generally, this thawing is at temperatures below 15° C. but above 0° C., over a time period sufficient to achieve complete thawing of the plasma 120, for example, the time period may be at least 4 hours, and may be up to 24 hours or even longer, if needed. A typical thawing would be carried out at 2-8° C. over a period of 6 to 12 hours. Plasma units that have a pink or red color are not selected for this preparation to ensure that the product is as free of hemoglobin as possible. During cold ("cryo") thawing of plasma, the dissolved high molecular weight components become solids 122 and fall ("precipitate") out of the plasma 124 into the bottom of the bag. This process is referred to as "cryo-precipitation".

Generally, the plasma contains various proteins which can be classified as low molecular weight (albumin-rich) proteins and high molecular weight proteins. While there is some variation in reported molecular weight for each protein, as used herein the low molecular weight proteins are ones that have a molecular weight range from 30-100 kDa, and high molecular weight proteins are that primarily extend above 100 kDa. For example, clotting factor VIII is reported to have a molecular weight from 90 to over 200 kDa, and would be considered high molecular weight because the majority of this range is over 100 kDA. For simplicity, as used herein, low molecular weight proteins can be considered those with molecular weights of less than 90 kDa, and high molecular weight proteins can be considered those with molecular weights of 90 kDa or greater. However, as used herein “high molecular weight proteins” includes at least fibrinogen (about 340 to 420 kDa), clotting factor VIII (about 90 to about 200 kDa), fibronectin (about 440 to 530 kDa), clotting factor XIII (about 320 kDa), and von Willebrand factor (about 800 to 20,000 kDA). The precipitate may also contain other proteins.

Thawed units are removed from the refrigerator and centrifuged 126 sufficiently to ensure that cryo-precipitates 122 are packed to the bottom of the bag. For example, the thawed units can be centrifuged at about 4500 RPM for about 8 minutes. After centrifugation, cryo-precipitates 122 are separated from plasma 124 by applying external pressure with a press, forcing plasma into empty bag 128, leaving behind the fibronectin-rich precipitates 130.

Figure 2:
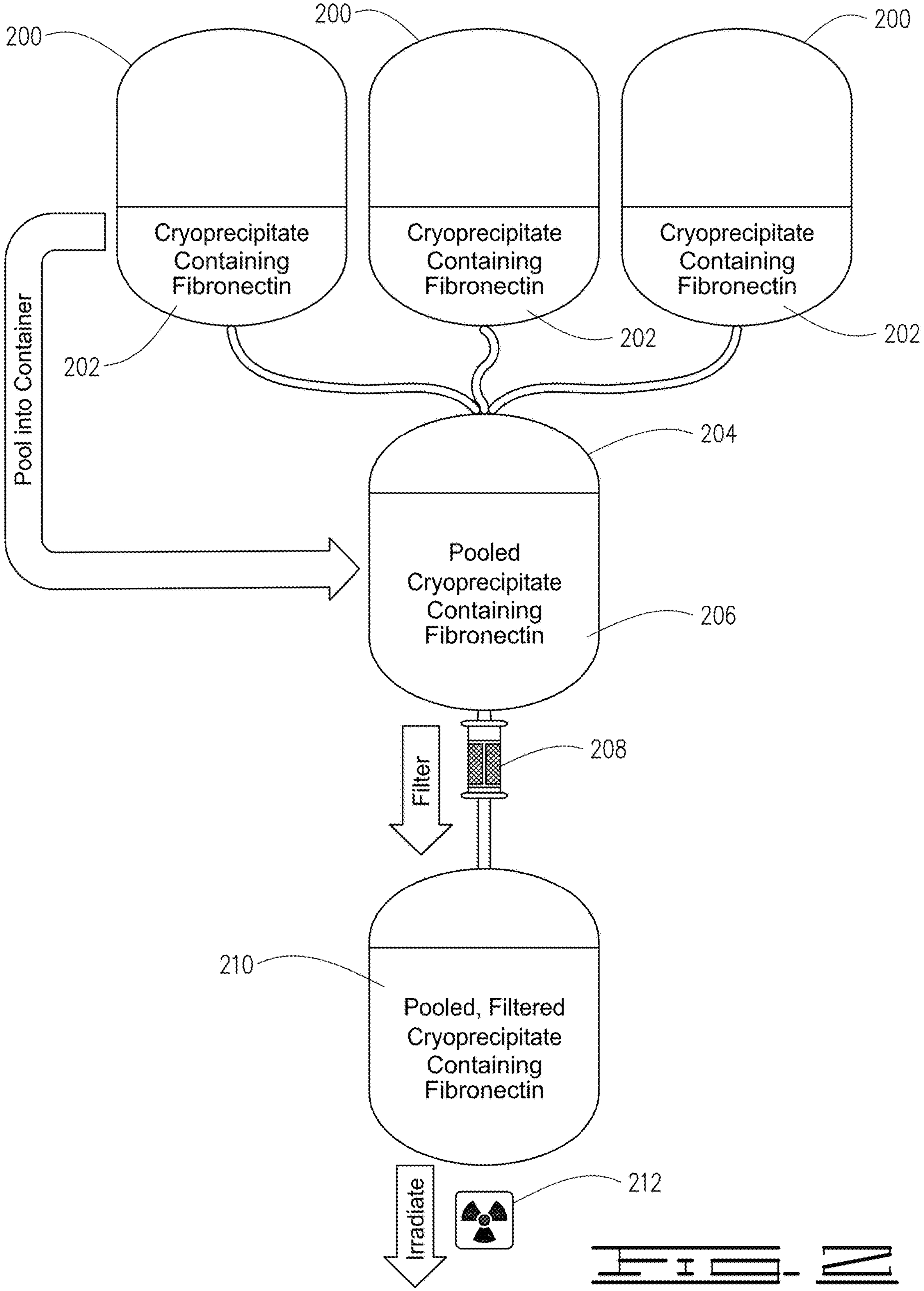
FIG. 2 is a schematic of preparing pooled, filtered, and irradiated fibronectin-rich material.

Turning now to FIG. 2, a method of preparing pooled, filtered and irradiated fibronectin-rich material is schematically illustrated. Multiple bags 200 of fibronectin-rich precipitates 202 are placed in a press to isolate the fibrinogen concentrate and pool them into a single container 204. Any number of bags can be pooled together. While the minimum number of bags in a pool is two, there is no maximum number. The press pools the fibrinogen concentrates by apply pressure to transfer them through tubing to container 204.

The pooled, fibronectin concentrate 206 is filtered 208. Filtration removes fibrinogen clumps and other aggregates that are not desired in the filtered product 210. The filtered product 210 is exposed to a radiation source 212 sufficient to inactivate bacteria, fungi, and extracellular viruses. By “inactivate” it is mean that the bacteria, fungi and extracellular viruses no longer reproduce or grow. For example, the radiation can be gamma irradiation or X-ray radiation that delivers around 50 Gy to the center of the product.

Figure 3:
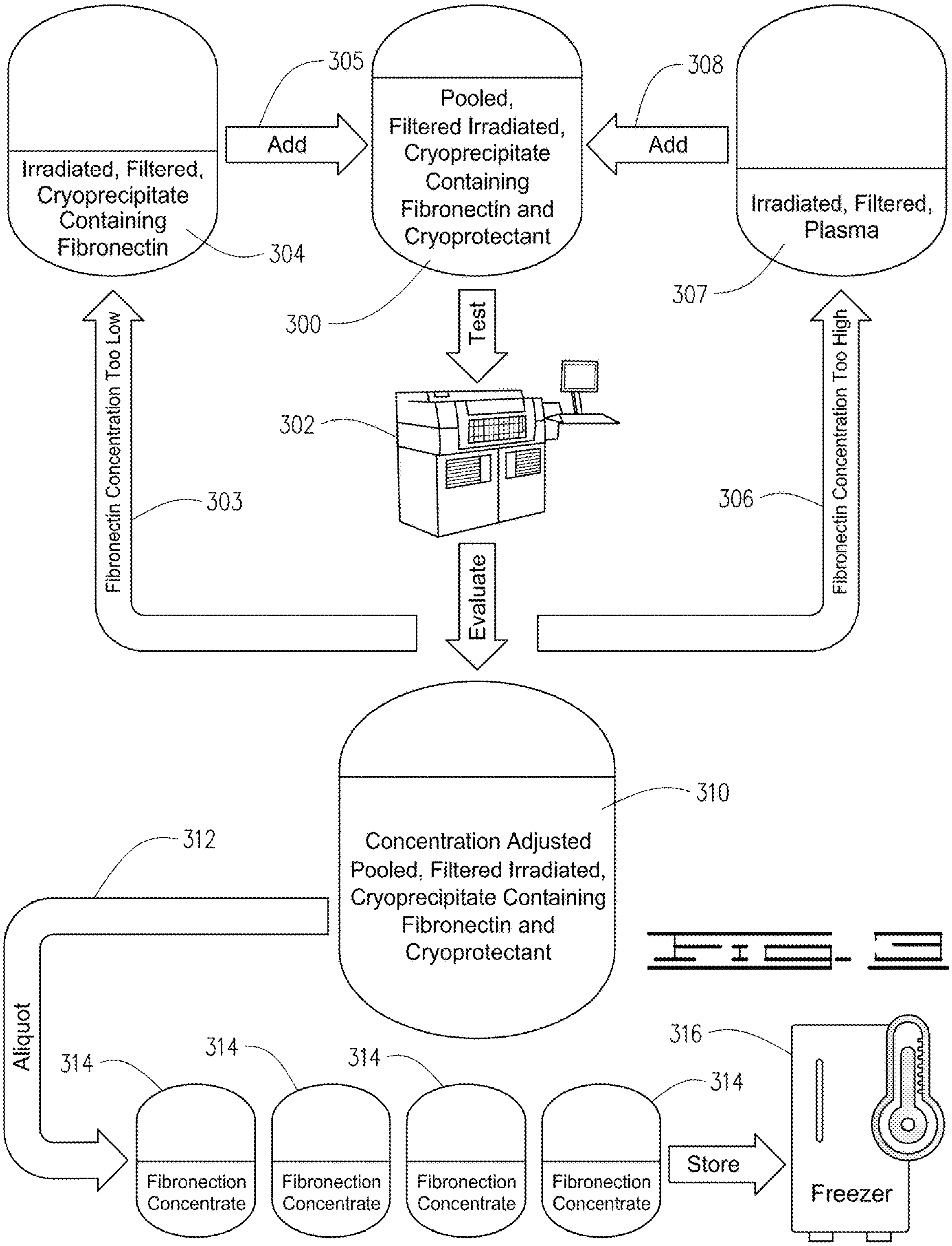
FIG. 3 is a schematic of preparing, cryopreserving, optimizing, and aliquoting fibronectin-rich material.

With reference to FIG. 3, a method of preparing, cryopreserving, optimizing and aliquoting fibronectin-rich material is schematically illustrated. Fibronectin levels in the pooled, filtered and irradiated cryoprecipitate 300 (sometimes referred to as the “irradiated concentrate” or “fibronectin concentrate pool”) are measured in step 302, such as by a commercially available ELISA colorimetric sandwich immunoassay, for example, the assay available from Enzo Life Sciences. This allows the fibronectin concentration to be optimized. For example, the optimized concertation can be from about 1 to about 5 mg/mL. If the concentration is too low (below a first threshold concentration), then filtered, irradiated cryoprecipitate AHF 304 is added to the fibronectin concentrate pool 300, as indicated by arrows 303 and 305. If the fibronectin level is too high (above a second threshold concentration), then filtered, irradiated plasma 307 is added to the fibronectin pool 300, as indicated by arrows 306 and 308. As will be realized from the forgoing, the irradiated cryoprecipitate AHF 304 and irradiated plasma 307 have been irradiated sufficiently to inactivate bacteria, fungi and extracellular viruses. The desired fibronectin concentration can vary from customer to customer; therefore, batches may have different optimal fibronectin levels and the volume of added irradiated cryoprecipitate AHF or irradiated plasma may differ.

Filtered, irradiated, and concentration-adjusted pools 310 are aliquoted (as indicated by arrow 312) into small volumes of fibronectin concentrate 314. For example, the irradiated pool can be aliquoted into separate units having a volume of from 1 mL to 100 mL and a fibronectin concentration of ranging from 1 mg/mL to 5 mg/mL. The final product is transferred and stored in a freezer 316, typically colder than 20° C., until ready for use. For example, the final product can be stored from 20° C. to −40° C.

Embodiments of the invention can be further understood by the following numbered paragraphs.

1. A method of preparing a pool of cryoprecipitate antihemolytic factor (AHF) from plasma precipitates, the method comprising:
   combining high molecular weight proteins to form a heterogenous pool of high molecular weight proteins, wherein the high molecular weight proteins are from a plurality of plasma units have been chill treated such that high molecular weight proteins precipitate out of the plasma units, wherein each plasma unit is from a different donor, and wherein the high molecular weight proteins include fibronectin and fibrinogen;
   filtering the heterogenous pool to remove at least a portion of the fibrinogen; and irradiating the heterogenous pool to produce the pool of cryoprecipitate anti-hemolytic factor (AHF) containing a concentration of fibronectin, wherein the irradiation is sufficient to inactivate bacteria, fungi, and extracellular viruses.
2. The method of paragraph 1, wherein the pool is used to generate a 3-dimensional matrix to promote the adhesion of cells in cultures.
3. The method of either paragraph 1 or paragraph 2, further comprising:
   after irradiation, adjusting the concentration of the fibronectin in the irradiated pool.
4. The method of any preceding paragraph, wherein the adjusting the concentration comprises:
   measuring the concentration of fibronectin levels contained in the irradiated pool, and
   if the measured concentration is below a first threshold concentration, adding irradiated cryoprecipitate AHF to the pool; and
   if the measured concentration is above a second threshold concentration, adding irradiated plasma to the pool, and
   wherein the irradiated cryoprecipitate AHF and irradiated plasma have been irradiated sufficiently to inactivate bacteria, fungi, and extracellular viruses.
5. The method of paragraph 4, wherein after adjusting the concentration, the irradiated pool is aliquoted into separate units having a volume of from 1 mL to 100 mL and a fibronectin concentration of ranging from 1 mg/mL to 5 mg/mL.
6. The method of any preceding paragraph, wherein the chill treatment comprises:
   providing a plurality of frozen plasma units which are at a freezing temperature at or below about −20° C.; and
   thawing the frozen plasma units under a refrigeration temperature of from about 15° C. to about 0° C. and for a time period sufficient to achieve complete thawing of the plasma.
7. The method of paragraph 6, wherein the freezing temperature is from about −20° C. to about −100° C.
8. The method of either paragraph 6 or paragraph 7, wherein the time period is from 4 hours to 24 hours.

9. The method of either paragraph 6 or paragraph 7, wherein the refrigeration temperature is from about 2° C. to about 8° C. and the time period is from about 6 hours to about 12 hours.

10. The method of any of paragraphs 6 to 9, wherein the frozen plasma units are obtained from plasma derived from a whole blood (WB) unit or an apheresis procedure, which are then frozen to a temperature of about −20° C. or less.

What is claimed is:

1. A method of preparing a fibronectin concentrate, comprising:

combining a plurality of chill treated plasma precipitates comprising fibronectin and fibrinogen, each plasma precipitate obtained from a different donor, to form a heterogeneous pool;

filtering the heterogeneous pool to remove at least a portion of the fibrinogen; and irradiating the filtered heterogeneous pool to produce the fibronectin concentrate comprising a concentration of fibronectin, wherein irradiating inactivates bacteria, fungi, and extracellular viruses, and wherein the fibronectin concentrate is used to generate a 3-dimensional matrix to promote adhesion of cells in cultures.

2. The method of claim 1, further comprising:

after irradiating, adjusting the concentration of the fibronectin in the fibronectin concentrate.

3. The method of claim 2, wherein adjusting the concentration comprises: measuring an amount of fibronectin in the fibronectin concentrate, and if the amount is below a first threshold, adding irradiated cryoprecipitate anti-hemolytic factor (AHF) to the fibronectin concentrate; or if the amount is above a second threshold, adding irradiated plasma to the fibronectin concentrate, wherein the irradiated cryoprecipitate AHF and the irradiated plasma have been irradiated to inactivate bacteria, fungi, and extracellular viruses.

4. The method of claim 3, further comprising, after adjusting the concentration, aliquoting the fibronectin concentrate into separate units having a volume from 1 mL to 100 mL and a fibronectin concentration from 1 mg/ml to 5 mg/mL.

5. The method of claim 1, wherein the chill treated plasma precipitates are produced by:

providing a plurality of frozen plasma units which are at a freezing temperature at or below about −20° C.; and thawing the plurality of frozen plasma units at a refrigeration temperature from about 0° C. to about 15° C. until completely thawed.

6. The method of claim 5, wherein the freezing temperature is from about −20° C. to about −100° C.

7. The method of claim 5, wherein thawing the plurality of frozen plasma units takes from 4 hours to 24 hours.

8. The method of claim 5, wherein the refrigeration temperature is from about 2° C. to about 8° C. and thawing the plurality of frozen plasma units takes from about 6 hours to about 12 hours.

9. The method of claim 5, wherein the frozen plasma units are obtained from plasma derived from a whole blood (WB) unit or an apheresis, procedure and frozen to a temperature of about −20° C. or less.

10. The method of claim 9, further comprising:

after irradiating, adjusting the concentration of the fibronectin in the fibronectin concentrate.

11. The method of claim 10, wherein adjusting the concentration of the fibronectin comprises:

measuring an amount of fibronectin in the fibronectin concentrate, and if the amount is below a first threshold, adding irradiated cryoprecipitate anti-hemolytic factor (AHF) to the fibronectin concentrate; or if the amount is above a second threshold, adding irradiated plasma to the fibronectin concentrate, wherein the irradiated cryoprecipitate AHF and the irradiated plasma have been irradiated to inactivate bacteria, fungi, and extracellular viruses.

12. The method of claim 11, wherein after adjusting the concentration, the fibronectin concentrate is aliquoted into separate fibronectin concentrate units having a volume from 1 mL to 100 mL and a fibronectin concentration of ranging from 1 mg/ml to 5 mg/mL.

13. The method of claim 12, wherein the separate fibronectin concentrate units are used to generate the 3-dimensional matrix to promote the adhesion of cells in cultures.

14. The method of claim 13, wherein the freezing temperature is from about −20° C. to about −100° C., and the refrigeration temperature is from about 2° C. to about 8° C. and the plurality of frozen plasma units takes from about 6 hours to about 12 hours.

15. A method of producing a fibronectin concentrate having a fibronectin concentration from about 1 mg/mL to about 5 mg/mL, comprising:

(i) combining a plurality of cryoprecipitate anti-hemolytic factor (AHF) produced by chill treating a plurality of plasma units to produce a pooled cryoprecipitate, wherein each cryoprecipitate AHF of the plurality of cryoprecipitate AHF comprises fibronectin and aggregates;

(ii) filtering the pooled cryoprecipitate to remove at least a portion of the aggregates to produce a filtered, pooled cryoprecipitate;

(iii) irradiating the filtered, pooled cryoprecipitate to produce an initial fibronectin concentrate, wherein irradiating inactivates bacteria, fungi, and extracellular viruses;

(iv) measuring the fibronectin concentration of the initial fibronectin concentrate; and (v) adjusting the fibronectin concentration of the initial fibronectin concentrate, wherein:

if the fibronectin concentration of the initial fibronectin concentrate is less than 1 mg/mL, a solution consisting of filtered, irradiated cryoprecipitate AHF having a greater fibronectin concentration than the initial fibronectin concentrate is added to the initial fibronectin concentrate to produce the fibronectin concentrate; or if the fibronectin concentration of the initial fibronectin concentrate is greater than 5 mg/mL, a solution consisting of filtered, irradiated plasma is added to the initial fibronectin concentrate to produce the fibronectin concentrate, and wherein the solution consisting of filtered, irradiated cryoprecipitate AHF and the solution consisting of filtered, irradiated plasma were previously irradiated to inactivate bacteria, fungi, and extracellular viruses, thereby producing the fibronectin concentrate having a fibronectin concentration from about 1 mg/mL to about 5 mg/mL.

16. The method of claim 15, further comprising, after adjusting, aliquoting the fibronectin concentrate into separate fibronectin concentrate units having a volume from 1 mL to 100 mL and a fibronectin concentration from 1 mg/mL to 5 mg/mL.

17. The method of claim 15, wherein chill treating a plurality of plasma units comprises:

providing a plurality of frozen plasma units at a freezing temperature at or below about −20° C.; and thawing the plurality of frozen plasma units at a refrigeration temperature greater than 0° C. to about 15° C. until completely thawed.

18. The method of claim 17, wherein the refrigeration temperature is from about 2° C. to about 8° C. and thawing the plurality of frozen plasma units takes from about 6 hours to about 12 hours.

* * * * *